US009288915B2

(12) United States Patent
Tai et al.

(10) Patent No.: US 9,288,915 B2
(45) Date of Patent: Mar. 15, 2016

(54) IC-PROCESSED POLYMER NANO-LIQUID CHROMATOGRAPHY SYSTEM ON-A-CHIP AND METHOD OF MAKING IT

(71) Applicants: City of Hope, Duarte, CA (US); California Institute of Technology, Pasadena, CA (US)

(72) Inventors: Yu-Chong Tai, Pasadena, CA (US); Qing He, Rancho Palos Verdes, CA (US); Jun Xie, Niskayuna, NY (US); Changlin Pang, Pasadena, CA (US); Terry D. Lee, San Dimas, CA (US); Damien Rodger, South Pasadena, CA (US); Matthieu Liger, San Francisco, CA (US)

(73) Assignees: CALIFORNIA INSTITUTE OF TECHNOLOGY, Pasadena, CA (US); CITY OF HOPE, Duarte, CA (US)

(*) Notice: Subject to any disclaimer, the term of this patent is extended or adjusted under 35 U.S.C. 154(b) by 0 days.

(21) Appl. No.: 13/680,030

(22) Filed: Nov. 17, 2012

(65) Prior Publication Data
US 2013/0140270 A1 Jun. 6, 2013

Related U.S. Application Data

(60) Division of application No. 13/037,192, filed on Feb. 28, 2011, now Pat. No. 8,323,488, which is a continuation of application No. 12/111,159, filed on Apr. 28, 2008, now abandoned, which is a
(Continued)

(51) Int. Cl.
*G01N 30/60* (2006.01)
*G01N 27/26* (2006.01)
(Continued)

(52) U.S. Cl.
CPC .......... *H05K 3/284* (2013.01); *G01N 30/6047* (2013.01); *G01N 30/6095* (2013.01); *G03F 1/80* (2013.01); *G01N 2030/645* (2013.01)

(58) Field of Classification Search
None
See application file for complete search history.

(56) References Cited

U.S. PATENT DOCUMENTS 5,116,495 A * 5/1992 Prohaska ............... 210/198.2
6,945,116 B2 9/2005 Xie et al.
(Continued)

FOREIGN PATENT DOCUMENTS

EP 1 065 378 A 1/2001
WO WO-98/07069 A 2/1998
(Continued)

OTHER PUBLICATIONS

Böhm et al., "A Closed-loop Controlled Electrochemically Actuated Micro-dosing System," Journal of Micromechanics and Microengineering, 10 (2000) 498-504.
(Continued)

*Primary Examiner* — Krishnan S Menon
(74) *Attorney, Agent, or Firm* — The Marbury Law Group, PLLC

(57) ABSTRACT

Embodiments in accordance with the present invention relate to packed-column nano-liquid chromatography (nano-LC) systems integrated on-chip, and methods for producing and using same. The microfabricated chip includes a column, flits/filters, an injector, and a detector, fabricated in a process compatible with those conventionally utilized to form integrated circuits. The column can be packed with supports for various different stationary phases to allow performance of different forms of nano-LC, including but not limited to reversed-phase, normal-phase, adsorption, size-exclusion, affinity, and ion chromatography. A cross-channel injector injects a nanoliter/picoliter-volume sample plug at the column inlet. An electrochemical/conductivity sensor integrated at the column outlet measures separation signals. A self-aligned channel-strengthening technique increases pressure rating of the microfluidic system, allowing it to withstand the high pressure normally used in high performance liquid chromatography (HPLC). On-chip sample injection, separation, and detection of mixture of anions in water is successfully demonstrated using ion-exchange nano-LC.

14 Claims, 14 Drawing Sheets

Related U.S. Application Data continuation of application No. 10/917,257, filed on Aug. 11, 2004, now abandoned.

(60) Provisional application No. 60/496,964, filed on Aug. 20, 2003.

(51) Int. Cl.
    *H05K 3/28*     (2006.01)
    *G03F 1/80*     (2012.01)
    *G01N 30/64*     (2006.01)

(56) References Cited

U.S. PATENT DOCUMENTS

| | | | |
|---|---|---|---|
| 7,090,471 B2 | 8/2006 | Xie et al. | |
| 7,254,008 B2 | 8/2007 | Xie et al. | |
| 2003/0027354 A1 | 2/2003 | Geli | |
| 2003/0228411 A1 | 12/2003 | Tai et al. | |
| 2004/0124085 A1 | 7/2004 | Tai et al. | |
| 2004/0253123 A1* | 12/2004 | Xie et al. | 417/410.1 |
| 2006/0193748 A1 | 8/2006 | Tai et al. | |

FOREIGN PATENT DOCUMENTS

| | | |
|---|---|---|
| WO | WO-00/30167 A | 5/2000 |
| WO | WO-03/081968 A | 10/2003 |
| WO | WO-2004/002878 A | 1/2004 |

OTHER PUBLICATIONS

Ceriotti et al., "An integrated fritless column for on-chip capillary electrochromatography with conventional stationary phases", *Anal. Chem.*, 2002, 74, 639-647.

Demello, "On-chip chromatography: the last twenty years", Lab on a Chip2, 48n-54n (2002).

Harris, "Shrinking the LC Landscape", Analytical Chemistry, Feb. 1, 2003, pp. 64A-69A.

He et al., "Fabrication of nanocolumns for liquid chromatography", *Anal. Chem.*, 70, 3790-3797, (1998).

He et al., "Parylene Neuro-Cages for Live Neural Networks Study", the 12th International Conference on Solid-State Sensors, Actuators and Microsystems (Transducers'03), Boston, MA, Jun. 8-12, 2003, pp. 995-998.

Liger et al., "Robust Parylene-to-Silicon Mechanical Anchoring", the 16th IEEE International Conference on Micro-Electro-Mechanical Systems (MEMS '03), Kyoto, Japan, Jan. 2003, pp. 602-605.

Manz et al., "Design of an open-tubular column liquid chromatography using silicon chip technology", *Sensors and Actuators B1*, 249-255 (1990).

Meng et al., "A Parylene MEMS Flow Sensing Array", Transducers 2003, Boston, MA, USA, Jun. 2003.

Meng et al., "A MEMS Body Fluid Flow Sensor", µTAS', Monterey, California, USA, Oct. 2001.

Meyer, *Practical High Performance Liquid* Chromatography, John Wiley & Sons, pp. 310-311 (1999).

Murrihy et al., "Ion chromatography on-chip", *J. of Chromatography A*, 924, 233-238 (2001).

Ocvirk et al., "High performance liquid chromatography partially integrated onto a Silicon chip", *Analytical Methods and Instrumentation*, vol. 2 No. 2, 74-82 (1995).

O'Neill et al., "On-chip Definition of Picolitre Sample Injection Plugs for Miniaturized Liquid Chromatography", Journal of Chromatography A, 924 (2001) 259-263.

Thorsen et al., "Microfluidic Large-Scale Integration", Science 298: 580-584 (2002).

Shih et al., "Surface Micromachined and Integrated Capacitive Sensors for Microfluidic Applications", the 12th International Conference on Solid-State Sensors, Actuators and Microsystems (Transducers 2003), Boston, USA, Jun. 2003, pp. 381-391.

Xie et al., "Electrolysis-Based On-Chip dispensing system for ESI-MS", the 16th IEEE International MEMS Conference (MEMS '03), Kyoto, Japan, Jan. 19-23, 2003, pp. 443-446.

Xie et al., "Integrated Parylene Electrostatic Peristaltic Pump", the Seventh International Symposium on Micro Total Analysis System (µTAS 2003), Squaw Valley, California, USA, Oct. 2003.

Xie et al., "Integrated Surface Micromachined Mass Flow Controller", the 16th IEEE International Conference on MicroElectroMechanical Systems (MEMS 2003), Kyoto, Japan, Jan. 2003, pp. 20-23.

Xie et al., "Surface Micromachined Leakage Proof Parylene Check Valve", the 14th IEEE International Conference on MicroElectroMechanical Systems (MEMS '01), Inerlaken, Switzerland, Jan. 2001, pp. 539-542.

Wang et al., "A Normally Closed In-Channel Micro Check Valve", the 13th IEEE International Conference on Micro Electro Mechanical Systems (MEMS '00), Miyazaki, Japan, Jan. 23-27, 2000.

Wang et al., "A Parylene Micro Check Valve", the 12th IEEE International Conference on Micro Electro Mechanical Systems (MEMS '99), 1999.

Wang et al., "A Fully Integrated Shear Stress Sensor", the 10th International Conference on Solid-State Sensors, Actuators and Microsystems (Transducers '99), 1999.

Singh, A.K., et al., "Gradient-Elution Reversed-Phase Electrochromatography in Microchips", 7th International Conference on Miniaturized Chem. and Biochem. Anal. Syst., (Oct. 5-9, 2003),pp. 1163-1166???

EP Appl. No. 04 78 6516, Suppl. EPO Search Report, dated Feb. 13, 2009 (11 pages).

\* cited by examiner

Open Backside Holes (Mask1,2)

Pattern Frontside Oxide (Mask 3)
Pattern Au for Bonding Pads (Mask 4)
Pattern Pt/Ti (Mask 5)

Pattern Photoresist (Mask 6,7)

Use Photoresist as Mask to Pattern Oxide (Mask 8)
DRIE

Parylene Deposition

Pattern Parylene (Mask 8)
Remove Exposed Photoresist

DRIE Open Backside Holes
Acetone Release (Wafer Scale)

Coating, Patterning and Curing of SU-8 (Mask 9)
Dicing

Open Backside Holes (Mask 1,2)

Pattern Frontside Oxide (Mask 3)
Pattern Au for Bonding Pads (Mask 4)
Pattern Pt/Ti (Mask 5)

Pattern Photoresist (Mask 6,7)

Use Photoresist as Mask to Pattern Oxide
DRIE

Parylene Deposition

Pattern Parylene (Mask 8)
Remove Exposed Photoresist

Coating and Patterning SU-8 (Mask 9)

DRIE Open Backside Holes
Dissolve Photoresist with IPA/Acetone

~40 μm

IC-PROCESSED POLYMER NANO-LIQUID CHROMATOGRAPHY SYSTEM ON-A-CHIP AND METHOD OF MAKING IT

CROSS-REFERENCE TO RELATED PATENT APPLICATIONS

This application is a division of U.S. Ser. No. 13/037,192, filed Feb. 28, 2011, which is a continuation of U.S. Ser. No. 12/111,159, filed Apr. 28, 2008, now abandoned, which is a continuation of U.S. Ser. No. 10/917,257 filed Aug. 11, 2004, now abandoned, which claims priority to U.S. Provisional patent application No. 60/496,964 filed Aug. 20, 2003, each of which are incorporated by reference in their entireties herein for all purposes.

STATEMENT AS TO RIGHTS TO INVENTIONS MADE UNDER FEDERALLY SPONSORED RESEARCH OR DEVELOPMENT

Work described herein has been supported, in part, by the NSF CENS Center (Grant No. CCR 0121778), the NSF ERC Center at the California Institute of Technology (Grant No. EEC-9402726) and the National Institute of Health (grant No. R01RR06217). The United States Government has certain rights in the invention.

BACKGROUND OF THE INVENTION

Separation of chemicals is widely and routinely performed in lots of industries and research labs. Liquid Chromatography (LC), and especially High Performance Liquid Chromatography (HPLC), is one of the most powerful and versatile separation techniques.

Although LC column is normally made of capillary tubes due to fluidics limitations, the miniaturization of the column can actually improve separation performance. As shown in FIG. 15 where same separation chemistry applies, separated peak width is independent of column ID, while peak heights are larger for smaller columns and/or smaller beads.

Conventional LC systems are also typically expensive and bulky. The separation columns, being of utmost importance in LC system, are also expensive and need replacements after a certain times of usage (typically about 100 times). Sample and solvent consumption cost is also very high.

A miniaturized LC system could be cheaper, faster, and exhibit minimized sample and solvent consumption. The need/market for miniaturized LC system is huge. However, comparing to the intense interests in miniaturized electrophoresis system on-a-chip, little is published about miniaturizing LC system onto a single chip. Harris et al., "Shrinking the LC Landscape", *Analytical Chemistry*, pp. 64A-69A (February 2003), and de Mello, "On-chip chromatography: the last twenty years", *Lab on a Chip* 2, 48n-54n (2002), both of which are incorporated by reference herein for all purposes, provide an overview of efforts in this area.

The main obstacles to miniaturization of LC systems are the lack of (1) a process to integrate various components of an LC system onto a monolithic chip; (2) high-pressure microfluidics needed for pumping liquid through densely-packed beads column; and (3) an approach to easily and reliably pack and seal chromatography supports (micro-beads) into the on-chip column.

From the above, it is seen that structures for performing liquid chromatography on small scales are highly desirable.

BRIEF SUMMARY OF THE INVENTION

Design and embodiments in accordance with the present invention relate to packed-column nano-liquid chromatography (nano-LC) systems integrated on-chip, and methods for producing and using same. The microfabricated chip includes a column, frits/filters, an injector, and a detector, fabricated in a process compatible with those conventionally utilized to form integrated circuits. The column can be packed with supports for various different stationary phases to allow performance of different forms of LC, including but not limited to reversed-phase, normal-phase, adsorption, size-exclusion, affinity, and ion chromatography. A cross-channel injector injects a nanolitre/picolitre-volume sample plug at the column inlet. An electrochemical/conductivity sensor integrated at the column outlet measures separation signals. A self-aligned channel-strengthening technique increases pressure rating of the microfluidic system, allowing it to withstand the high pressure normally used in nano-high performance liquid chromatography (nano-HPLC). On-chip sample injection, separation, and detection of mixture of anions in water is successfully demonstrated using ion-exchange nano-LC.

An embodiment of method in accordance with the present invention for fabricating a liquid chromatography system, comprises, patterning a sacrificial material on a first side of a substrate to define a column region, forming an encapsulant over the first side of the substrate and the sacrificial material, and removing the sacrificial material to define a column. Access is then provided to an inlet of the column region and to an outlet of the column region.

An embodiment of a liquid chromatography apparatus in accordance with the present invention, comprises, a column defined between a substrate and a deposited Parylene layer, a column inlet in fluid communication with a first end of the column, and a column outlet in fluid communication with a second end of the column opposite the first end.

An embodiment of a method in accordance with the present invention for performing liquid chromatography, comprises, introducing a liquid sample at an inlet of a column defined between a deposited Parylene layer adhered to a substrate, flowing the sample down the column to an outlet, and detecting a changed property of the sample at the outlet.

Various additional features and advantages of the present invention can be more fully appreciated with reference to the detailed description and accompanying drawings that follow.

DETAILED DESCRIPTION OF THE INVENTION

As employed in this patent application, the term "nano-LC" refers to a liquid chromatography system employing a column inner diameter (ID) of less than 100 μm. Where such a nano-LC system is employed with a corresponding flow rate on the order of tens to hundreds of nL/min, the system is referred to as a "nano-HPLC system".

Embodiments in accordance with the present invention relate to packed-column nano-liquid chromatography (nano-LC) systems integrated on-chip, and methods for producing and using same. The microfabricated chip includes a column, flits/filters, an injector, and a detector, fabricated in a process compatible with those conventionally utilized to form integrated circuits. The column can be packed with supports for various different stationary phases to allow performance of different forms of nano-LC, including but not limited to reversed-phase, normal-phase, adsorption, size-exclusion, affinity, and ion chromatography. A cross-channel injector injects a nanolitre/picolitre-volume sample plug at the column inlet. An electrochemical/conductivity sensor integrated at the column outlet measures separation signals. A self-aligned channel-strengthening technique increases pressure rating of the microfluidic system, allowing it to withstand the high pressure normally used in high performance liquid chromatography (nano-HPLC). On-chip sample injection, separation, and detection of mixture of anions in water is successfully demonstrated using ion-exchange LC.

1. Overview

Figure 1A:
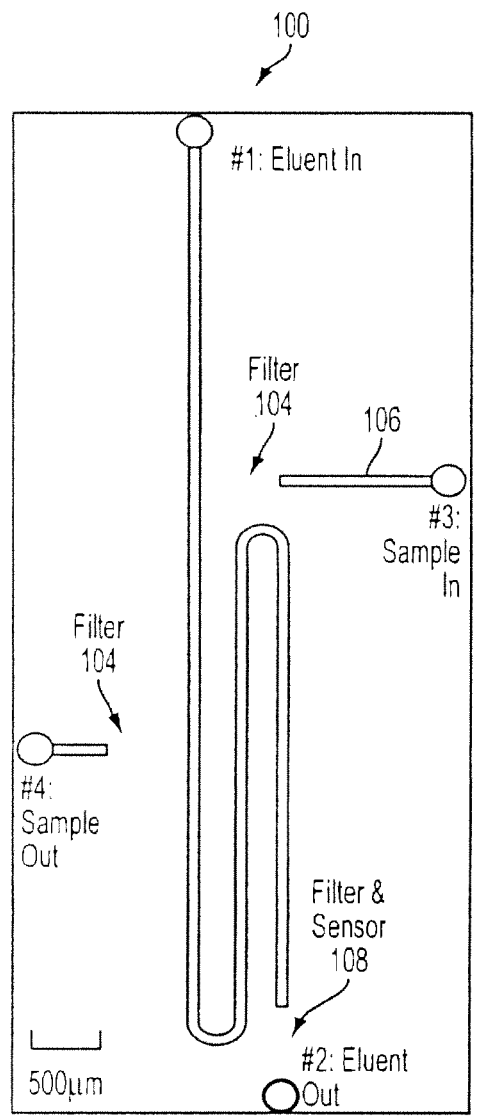
FIG. 1(a) shows a fluorescent top-view photograph of an embodiment of an integrated nano-LC system in accordance with the present invention, including column, filter/flits, on-chip injector and detector.
Figure 1B:
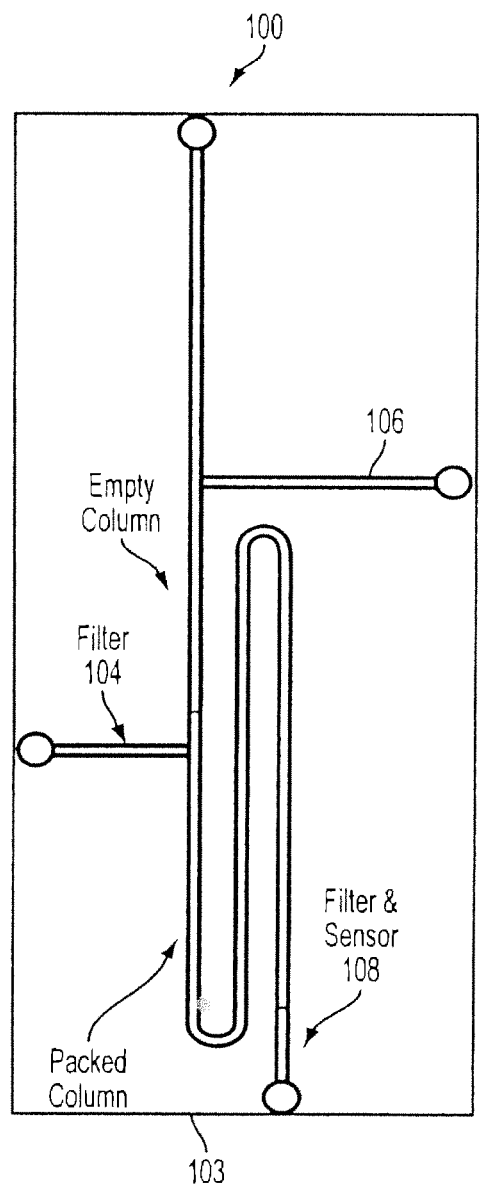
FIG. 1(b) shows an optical photograph of the nano-LC device of FIG. 1(a) after packing beads into the column.

FIG. 1(a) shows a fluorescent top-view photograph of one embodiment of an integrated nano-LC system in accordance with the present invention. Integrated nano-LC system 100 comprises column 102, filter/flits 104, on-chip injector 106, and detector/sensor 108. FIG. 1(b) shows an optical photograph of the nano-LC device of FIG. 1(b) after packing beads 103 into the column 102.

Figure 2A:
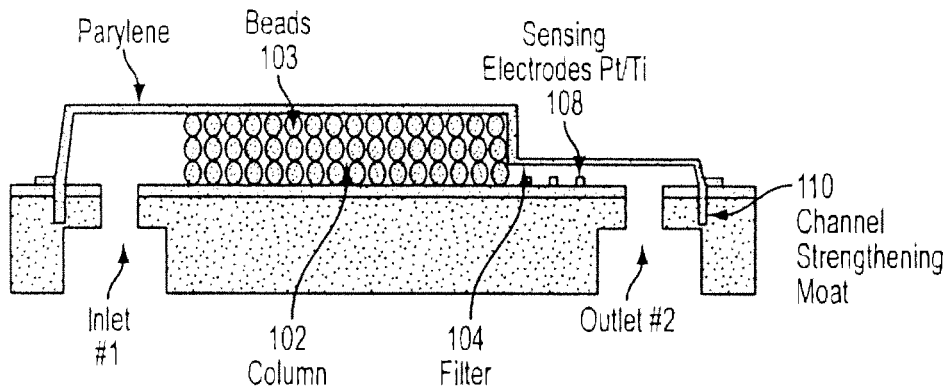
FIG. 2(a) illustrates a cross-sectional view of the nano-LC device of FIGS. 1(a)-(b).
Figure 2B:
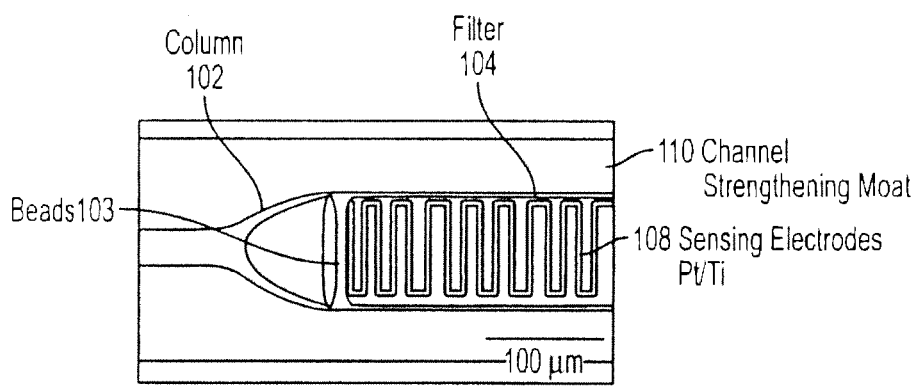
FIG. 2(b) shows a top view photograph of the nano-LC device of FIG. 2(a) including a packed column, a filter, sensing Pt/Ti electrodes, and channel strengthening moat.
Figure 2C:
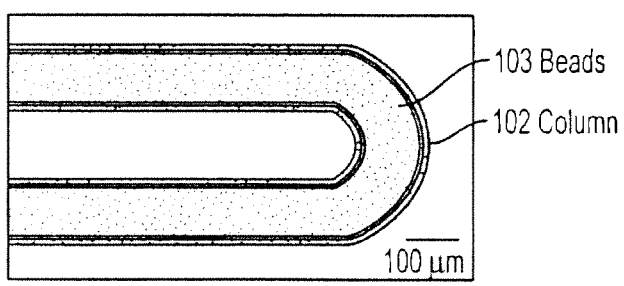
FIG. 2(c) shows a fluorescent picture of densely packed beads in an on-chip column.

FIG. 2(a) shows a cross-sectional view illustrating the nano-LC device of FIG. 1(a). FIG. 2(b) shows a top view picture of column 102 packed with 7 μm ion-exchange beads 103, filter 104, sensing Pt/Ti electrodes 108, and channel strengthening moat 110. FIG. 2(c) shows a fluorescent picture of densely packed beads 103 in an on-chip column 102.

Backside holes 112 provide channel inlet and outlet. Beads 103 are packed into the column 102 with the filters 104 at the column outlet to stop beads. The filter 104 holds beads in place because its openings are smaller than the diameter of the beads. In FIG. 2(b), it can be clearly seen that the beads 103 stop at the front of the filter 104.

The nano-LC-on-a-chip device of FIGS. 1(a)-(b) is made using integrated Parylene microfluidics. LC stationary-phase support material comprising micro-beads with functional groups, is packed externally into the on-chip column from the inlet port located at point #1.

The separation mobile phase is also pumped from point #1 to point #2. The column is serpentine in shape to maximize column length within an area of the chip occupied by the column. The beads-packed column outlet is at the filter/detector at point #2, and the column inlet is near the filter at point #4 to receive the injected plug front.

Nanolitre/picolitre volume sample injection is achieved with cross-channel injection from points #3 to #4. Such cross-channel injection is described in detail by O'Neill et al., "On-chip Definition of Picolitre Sample Injection Plugs for Miniaturized Liquid Chromatography", *Journal of Chromatography A*, 924, 259-263 (2001), incorporated by reference herein for all purposes.

The integrated design shown in FIGS. 1(a)-(b) minimizes dead volume, thus reducing extra-column peak broadening. Filters 104 and channels 102 with height smaller than the bead's diameter, near points #3 and #4 prevent the beads from entering the side channels.

To anchor Parylene channels, a "moat" surrounding channels is subjected to deep reactive ion etching (DRIE) and/or roughened with $XeF_2$, then filled with Parylene. Fabrication of the moat is discussed below.

As shown in FIGS. 2(a)-(b), conductivity sensor 115 is used as the detector for ion sensing. Interdigital electrodes 108 are patterned in the detector cell 115 to monitor liquid conductivity. The conductivity of the mobile phase solution provides a baseline signal. When separated ion plugs pass by the detector, changes of solution conductivity are detected. Chromatogram is then obtained by recording conductivity of the solution flowing in the detection cell over time.

To increase sensitivity, electrode width and spacing should be small, and the total electrode area should be maximized.

However, the electrode design should be compromised in considerations of minimizing peak broadening and multiple-peak detection.

Off-chip pumping is used for mobile phase delivery and sample injection. On-chip pumps can be integrated if necessary. A detailed discussion of integrated on-chip gradient-generating micro-pumps is found in U.S. nonprovisional patent application Ser. No. 10/603,573, filed Jun. 24, 2003 and incorporated by reference herein for all purposes.

2. Fabrication

Figure 3A:
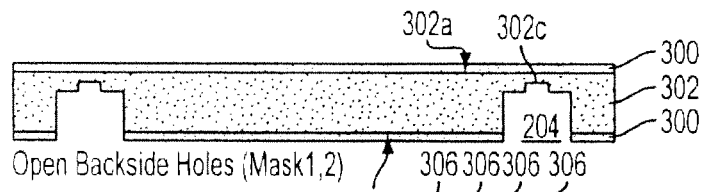
FIGS. 3(a)-(h) show simplified cross-sectional views of one embodiment of a process for fabricating a nano-LC system in accordance with the present invention.

FIGS. 3(a)-(h) show simplified cross-sectional views of one embodiment in accordance with the present invention of a process flow for fabricating the nano-LC device. As shown in FIG. 3(a), the fabrication process starts with growing thermal oxide 300 on both sides 302a and 302b of a silicon wafer 302. Then two-step DRIE is done on the backside 302b to etch the backside holes 304, leaving only a 50 μm-thick diaphragm 302c.

Figure 3B:
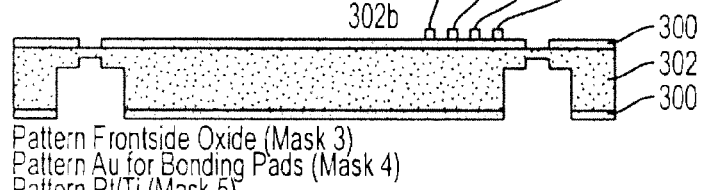

FIG. 3(b) shows the following frontside oxide patterning, followed by evaporation and patterning of 300 Å Ti/2000 Å Pt/1000 Å Au electrodes 306. Au is only for wire bonding purpose, since it is very difficult to directly bond to Pt. Therefore, Au is patterned to be only at bonding pads. Pt is the electrode for electrochemical/conductivity sensing, and is patterned with hot Aqua Regia (1 $HNO_3$:6HCl:3 $H_2O$ at 80° C.). Ti is used as adhesion layer between Pt and substrate.

Figure 3C:
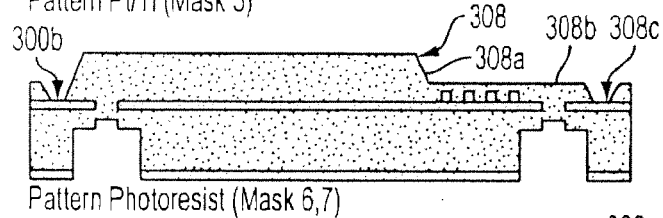

As shown in FIG. 3(c), 25 μm-thick photoresist AZ4620 is spun on the front side of the substrate and patterned with two masks to form two-level sacrificial structure 308. Unexposed areas 308a are for forming channels. Partially exposed areas 308b are for forming filters and/or for patterning oxide later. Fully exposed areas 308c reveal oxide 300b underneath.

Figure 3D:
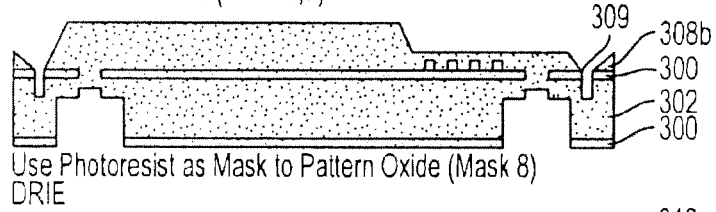

FIG. 3(d) shows the following stage in the fabrication process flow, wherein the oxide 300b revealed by development of the filly exposed areas is subsequently etched away with BHF. Next, DRIE masked by photoresist is performed on the front side to remove silicon and form trench moat 309. Alternatively, or in conjunction with DRIE of the exposed silicon during this step, $BrF_3$/$XeF_2$ may be used to roughen exposed silicon and thereby promote adhesion of the Parylene deposited in the next step.

Figure 3E:
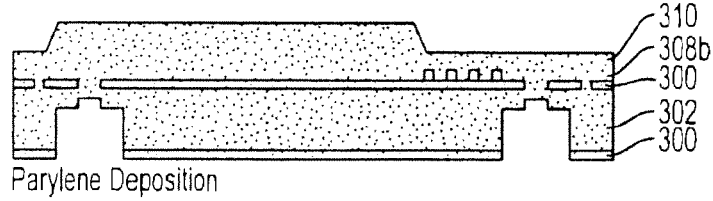

Next, as shown in FIG. 3(e), Parylene 310 is then deposited over the entire structure, including over the photoresist and within the moat area. As shown in this and the previous figure, formation of the trench moat and/or roughened silicon regions is masked by the existing photoresist, thereby constituting a self-aligned process. The self-aligned nature of this process eliminates the need for a separate masking step and enhances throughput.

Figure 3F:
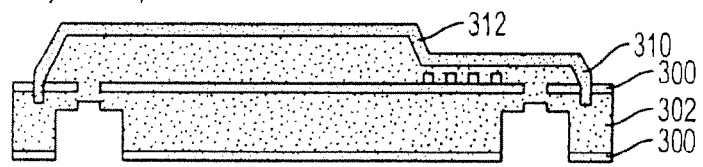

In FIG. 3(f), the Parylene deposited in FIG. 3(d) is patterned to form channels 312. Photoresist outside channels 312 is then stripped.

Figure 3G:
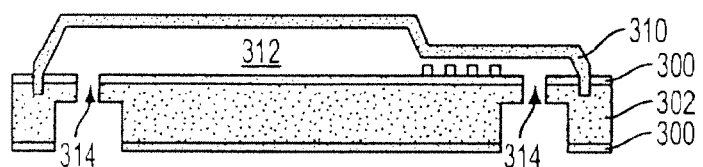

FIG. 3(g) then shows backside opening of access holes 314 with DRIE. Photoresist in the channels is then dissolved in Acetone, thus the channels 312 are released.

Figure 3H:
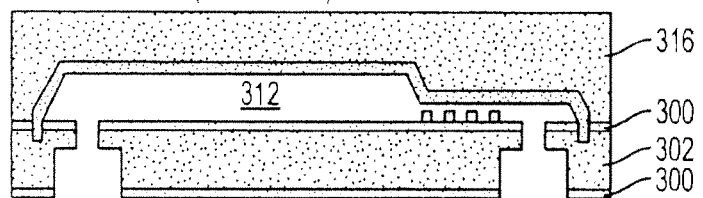

Finally, as shown in FIG. 3(h), an optional SU-8 layer 316 could be applied and patterned to further strengthen the channels.

Figure 4A:
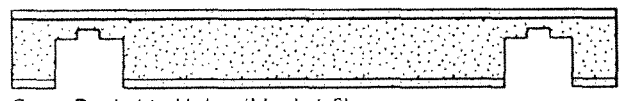
FIGS. 4(a)-(h) show simplified cross-sectional views of an alternative embodiment of a process for fabricating a nano-LC system in accordance with the present invention.
Figure 4B:
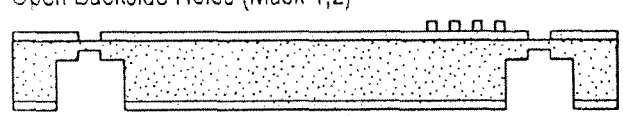
Figure 4C:
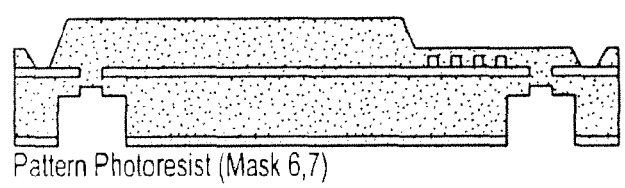
Figure 4D:
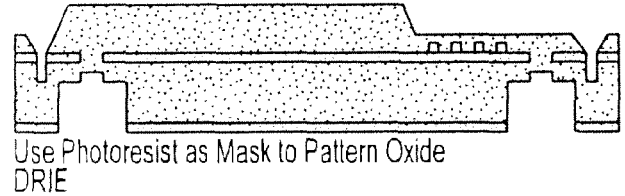
Figure 4E:
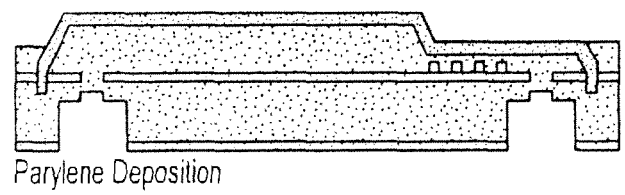
Figure 4F:
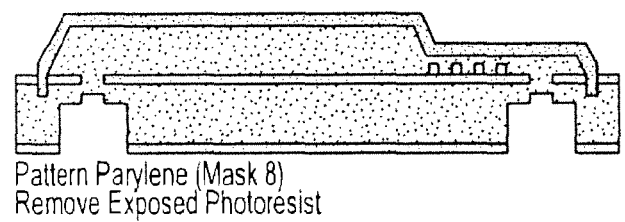
Figure 4G:
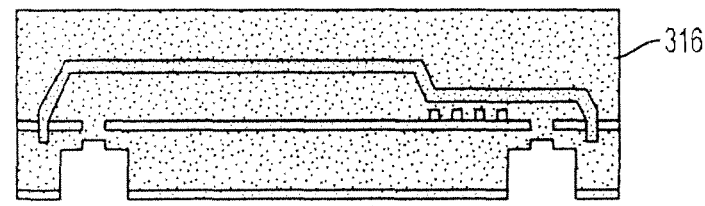
Figure 4H:
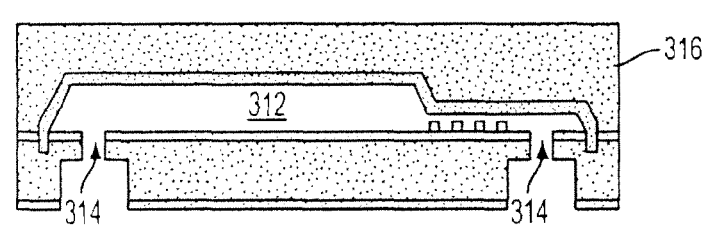

FIGS. 4(a)-4(h) show simplified cross-sectional views of an alternative process flow for forming a nano-LC system in accordance with embodiments of the present invention. FIGS. 4(a)-(f) are identical to corresponding FIGS. 3(a)-(f). FIGS. 4(g)-(h), however, illustrate that the SU-8 layer 316 can alternatively be applied before opening backside holes 314 and removal of photoresist.

Figure 16A:
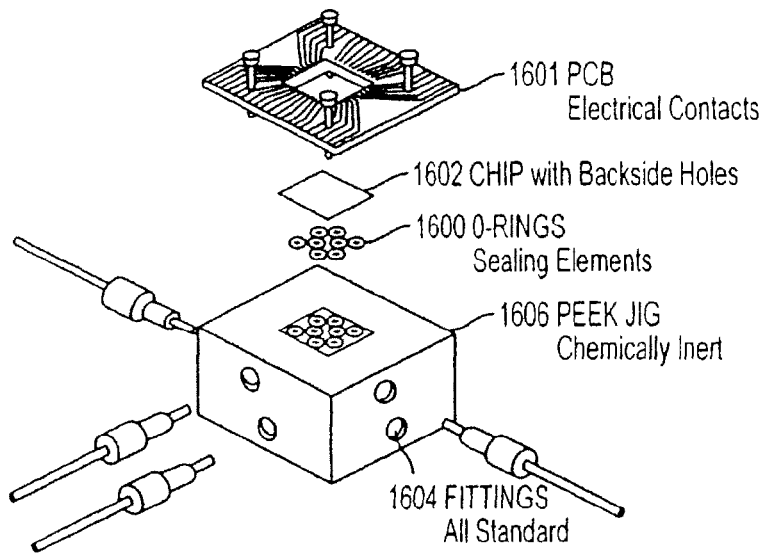
FIG. 16(a) shows an exploded view illustrating the parts of the testing jig.
Figure 16B:
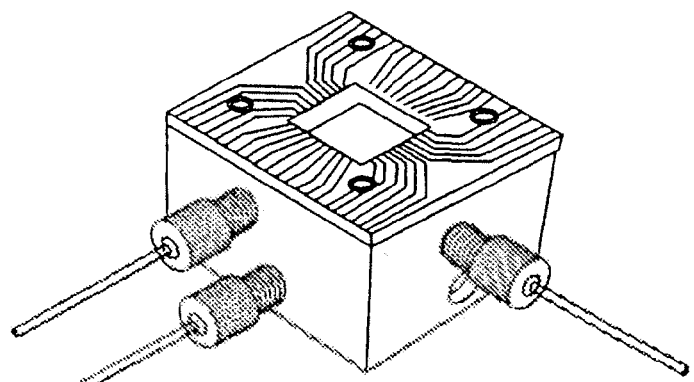
FIG. 16(b) shows a photograph of the assembled package.
Figure 16C:
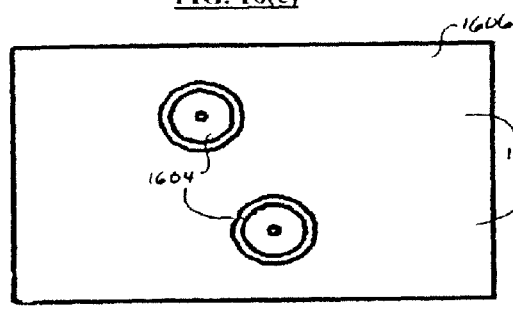
FIGS. 16(c)-(d) show simplified side views of the assembled package.
Figure 16D:
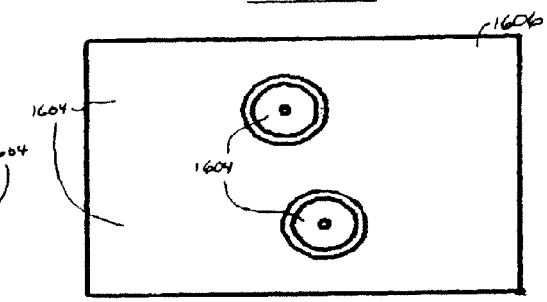
Figure 16E:
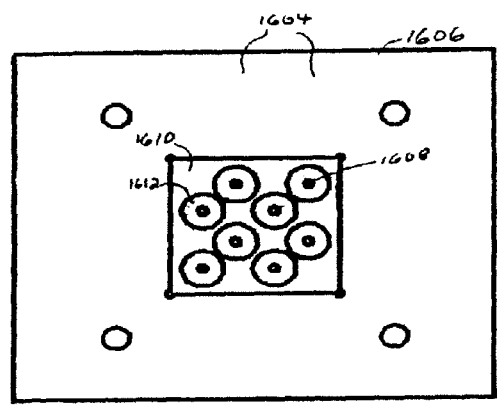
FIG. 16(e) shows a simplified plan view of the assembled package.
Figure 16F:
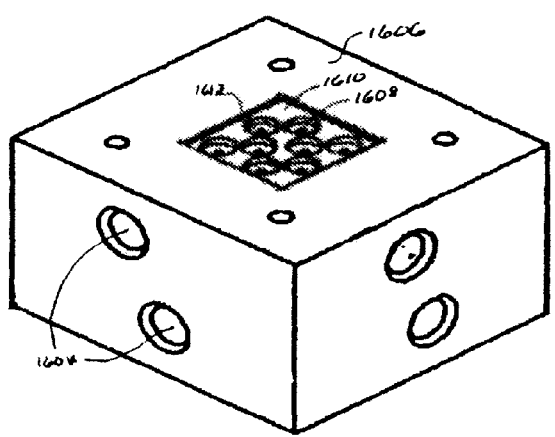
FIG. 16(f) shows a simplified perspective view of the assembled package.

FIG. 16(a) shows an exploded view illustrating the parts of a packaging jig developed for convenient testing of the chips, and can be used as a chip packaging method for real applications. FIG. 16(b) shows a photograph of the assembled package.

Specifically, FIGS. 16(a)-(b) show that the fabricated chip is clamped between a printed circuit board (PCB) 1601 and the PEEK jig 1606. Squeezed o-rings 1600 at chip 1602 backside provide sealing. While the specific embodiment of FIG. 16(a) includes o-rings as separate sealing elements, this is not required by the present invention. In accordance with alternative embodiments, the sealing element could comprise a polymer gasket layer.

Standard fining receiving ports 1604 are made in the jig 1606, so fluid connections with external sources are easily obtained. Electrical contacts are made by wire bonding from the on-chip Au pads to the PCB. The jig can access eight out of the sixteen holes (4×4) simultaneously on the chip.

FIGS. 16(c)-(f) show side, top, and perspective views illustrating additional details about the jig. The jig body 1606 is made of PEEK material, which is inert for most chemicals and solvents. Commercial fitting receiving ports are machined in the jig as the interface between the jig and the outside tubing with commercial fittings. Drilled holes in the jig lead fluid from the receiving ports to the jig top surface.

The jig top surface has two shapes of recesses. The square recess 1610 is used for holding the chip. The circular recesses 1612 are for o-rings.

There are eight holes 1608 in the square recess, which connects with the eight receiving ports 1604 on the four sides of the jig 1606. The holes 1608 are arranged so that by rotating the chip or jig by 90°, a different set of eight hole positions can be accessed. In this manner, a total of sixteen hole positions in the form of a 4×4 array can be accessed on the chip, with at most eight holes accessed simultaneously.

Figure 16G:
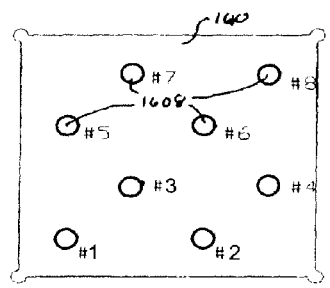
FIGS. 16(g)-(i) show schematic plan views illustrating the configuration of holes on the jig in various orientations.
Figure 16H:
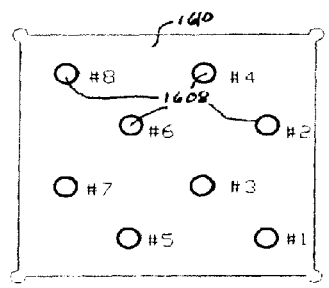
Figure 16I:
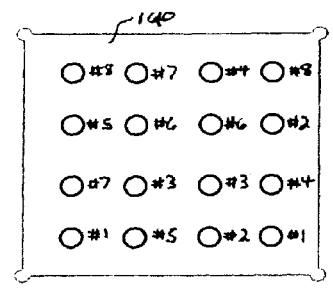

FIG. 16(g) shows the eight accessible hole positions in the original orientation of the jig. FIG. 16(h) shows the location of another eight hole positions accessible after a rotation of the jig 90° from the orientation of FIG. 16(g). FIG. 16(i) shows a composite of the jig orientations of FIGS. 16(g)-(h), illustrating that a 4×4 array of sixteen hole positions can be accessed, eight positions at a time.

As shown in the view of FIG. 16(b) depicting the assembled package, when the o-rings and chip are placed in their recesses, a top PCB (Printed Circuit Board) cover is placed on top and compresses chip and o-rings. The O-rings provide sealing between the chip and jig. Then electrical access to the chip is made by wire-bonding or even soldering from the chip to the top PCB.

Liquid chromatography system is known to be operating at very high pressures. Miniaturized on-chip nano-LC system can operate at much lower pressure since the column cross-sectional area and column length could be smaller. However, it would still be desirable to have at least 100 psi compatibility in order to perform High Performance Liquid Chromatography (nano-HPLC) on-chip.

Parylene to substrate adhesion is poor, which is usually improved by applying chemical adhesion layer (for example, A-174) on the substrate before Parylene deposition. And Parylene-to-Parylene adhesion is usually enhanced by roughing the bottom Parylene with oxygen plasma. Nevertheless, even with these techniques, Parylene channels on substrate or on Parylene, can still withstand pressure up to only about 30 psi. Above that pressure, top Parylene layer would delaminate from substrate or from bottom Parylene.

This value may be compared with that exhibited by PDMS devices described by Thorsen et al., in "Microfluidic Large-Scale Integration", Science 298: 580-584 (2002), incorporated by reference herein for all purposes, which are commonly used in microfluidic/µTAS area. Such PDMS devices can withstand pressure only up to a bit over 40 psi.

In "Robust Parylene-to-Silicon Mechanical Anchoring", *The 16th IEEE International Conference on Micro-Electro-Mechanical Systems*, Japan, pp. 602-605 (MEMS '03), incorporated by reference herein for all purposes, Liger et al. describe mechanical Parylene anchoring to the substrate. In "Parylene Neuro-Cages for Live Neural Networks Study", 12*th Intl Conf. on Solid-State Sensors, Actuators and Microsystems*, Boston, pp. 995-998 (Transducers '03), incorporated by reference herein for all purposes, He et al. also describe the use of this technique to anchor neuro-cages to substrate, which allows the neuro-cages to survive aggressive chemicals used in culturing experiments These experiences lead to the invention of a special channel-strengthening technique has been invented in the above processes to strongly anchor Parylene channels to the substrate, to increase pressure rating of the system. Specifically, a self-aligned channel-anchoring technique in accordance with embodiments of the present invention, uses a channel-surrounding moat that is self-aligned to the channel edges. The moat can be special trench into Si substrate made with modified DRIE process, or $BrF_3/XeF_2$ roughened Silicon.

Figure 5A:
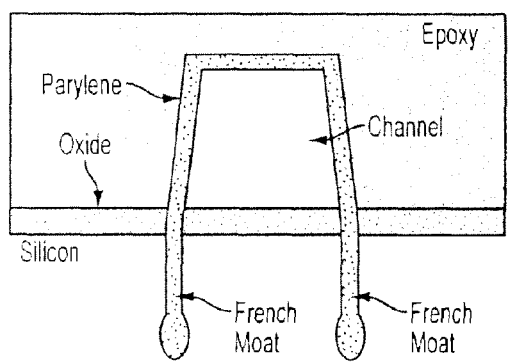
FIGS. 5(a)-(b) show cross-sectional views of Parylene channels made with different anchoring techniques in accordance with embodiments of the present invention.
Figure 5B:
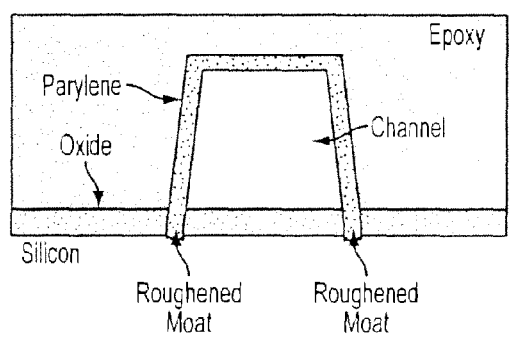

FIGS. 5(*a*) and 5(*b*) illustrate cross-sectional views of finished channels made with these two anchoring techniques, respectively. The trench of FIG. 5(*a*) is made with standard DRIE Bosch process followed by short time $SF_6$ isotropic etching to create the mushroom profile at the trench bottom.

Figure 6A:
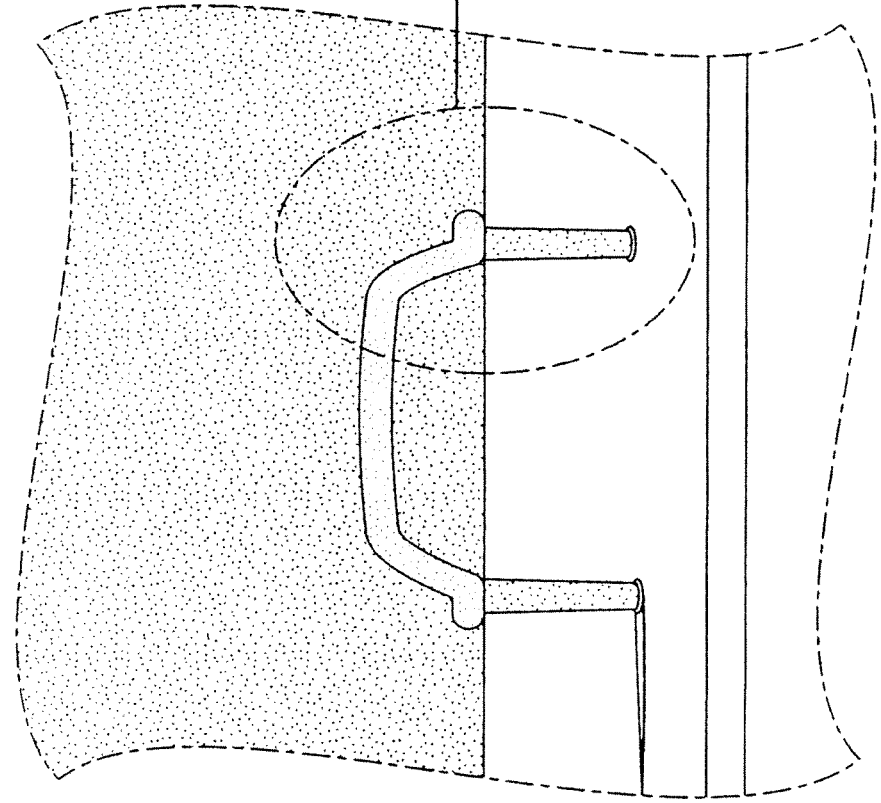
FIGS. 6(a)-(b) show cross-sectional photographs of a Parylene channel anchored with special trench with mushroom profile at the trench bottom.
Figure 6B:
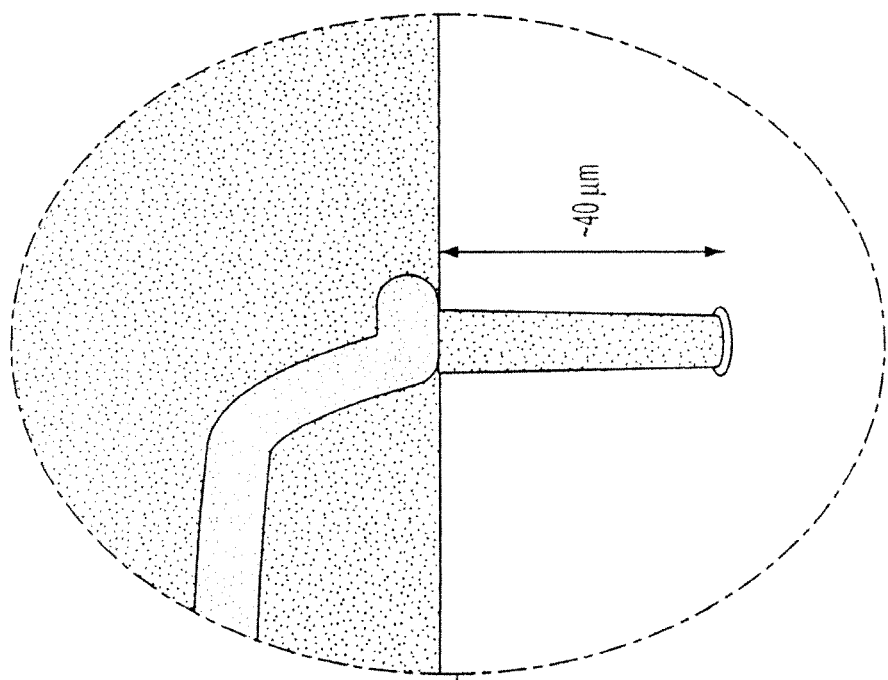

FIG. 6(*a*) shows a photograph of a cross-sectional view of a Parylene channel anchored with special trench with mushroom profile at the trench bottom, ~40 µm-deep.

FIG. 6(*b*) shows an enlarged view of a portion of the cross-section shown in FIG. 6(*a*).

Figure 7:
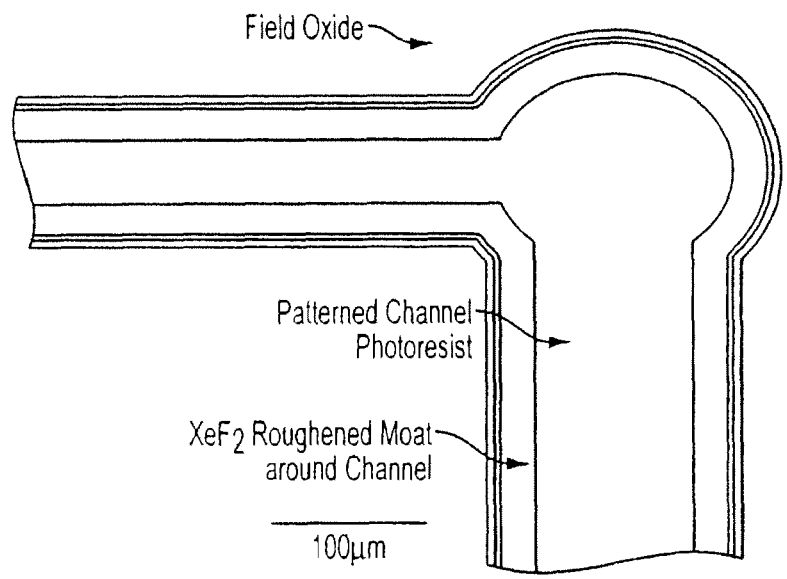
FIG. 7 shows a top view photograph of a $XeF_2$ roughened channel moat before Parylene deposition.

FIG. 7 is a top view photograph of an $XeF_2$ roughened moat surrounding patterned photoresist (channel sacrificial material) before Parylene deposition, for the second (channel roughening) strengthening approach shown above in FIG. 5(*b*).

3. Testing

To test the pressure limit of strengthened channels, a special testing channel having only one access hole (inlet) is used. Water is dropped over the channel, and pressurized $N_2$ gas is applied to the channel. Once the channel is broken, bubbles will leak out and show up as bubbles in water. Table 1 is the summary of the testing results.

TABLE I

| | Channel Strengthening Technique | | | |
| --- | --- | --- | --- | --- |
| | Roughening | Roughening + Epoxy | Trench | Trench + epoxy |
| Safe Pressure | 250 psi (>60 min) | 700 psi (>60 min) | 600 psi (>60 min) | 800 psi (>60 min) |
| Above Safe Pressure | Small Bubbles Appear | Small Bubbles Appear | No Bubble before Breaking | N/A |
| Breaking Pressure | ~350 psi | ~800 psi | ~700 psi | ~800 psi |

The safe pressures obtained are well above desired 100 psi, and the highest even reach 800 psi, which is limited by our testing setup. Embodiments of nano-LC systems in accordance with the present invention could be utilized with applied pressures of 1000 psi or greater in order to perform high performance liquid chromatography on a chip.

Instead of SU-8, epoxy is used to further strengthen the channels, as SU-8 is one kind of photopatternable epoxy. It is clear that trench anchoring technique provides superior anchoring performance to roughening. It should be noted that pressure limits obtained also depend on moat width, trench depth/shape, and parylene thickness.

The failure modes of the two anchoring techniques are also different. Roughening-anchored channels leak out working fluid through tiny tunnels in roughened moat area under high pressure, while trench-anchored ones don't leak at all until the Parylene breaks.

In terms of introduction and retaining nano-LC stationary phase materials into the column, several approaches have previously been proposed. In "Design of an open-tubular column liquid chromatography using silicon chip technology", *Sensors and Actuators B*1 249-255 (1990), Manz et al. describe an open-tubular approach. In "Fabrication of nano-columns for liquid chromatography", *Anal. Chem.* 70, 3790-3797 (1998), He et al. describe coating micromachined posts arrays. In "Ion chromatography on-chip", *J. of Chromatography A*, 924, 233-238 (2001), Murrihy et al. et al describe coating a microchannel with nanoparticles. In "Gradient-elution reversed-phase electrochromatography in microchips", *Proc. µTAS* 2003, pp. 1163-1166, Singh et al. describe a monolithic device. In "High performance liquid chromatography partially integrated onto a Silicon chip", *Analytical Methods and Instrumentation*, Vol. 2 No. 2, 74-82 (1995), Ocvirk et al describe a packing approach. In "An integrated fritless column for on-chip capillary electrochromatography with conventional stationary phases", *Anal. Chem.*, 2002, 74, 639-647, Ceriotti et al. describe an approach utilizing packing without a fit. Each of the above-referenced publications is hereby incorporated by reference for all purposes.

In accordance with embodiments of the present invention, a slurry packing technique is used to pack LC stationary phase support material (beads) into on-chip columns. First the beads are mixed with water or Isopropyl Alcohol, then a vortexer is used to homogenize the solution, also to prevent beads from precipitation. Then the solution is sucked into a syringe/pipette, and injected into a section of tubing as a beads solution reservoir. The tubing fill of beads/solution mixture is then switched on-line, and off-chip pressure source is used to pack the beads into the column on-chip. The pressure source can be simply pushing syringe manually, or a syringe pump or pressurize gas.

To get a uniform and dense packing, constant high pressure is preferred. The columns we used to do testing are all packed at 200 psi using pressurized $N_2$ gas. After the beads are packed, the beads bed won't flow back even when the inlet pressure is released.

In this work, packing with conventional beads is chosen because of the following advantages. First, without introducing new surface chemistry, the extensively established separation knowledge can be utilized. Secondly, extreme flexibility is there to perform different types of liquid chromatography and/or to optimize particular separations, by choosing bead type, size, pore size, porosity, and functional group. Thirdly, packed column can achieve reproducible column performance, which is usually a problem in other methods.

Figure 8:
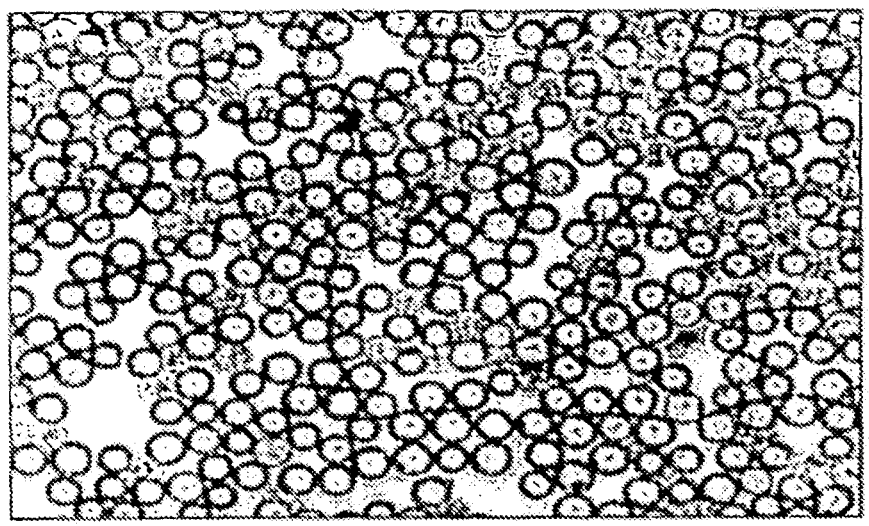
FIG. 8 shows a photograph of the beads used to pack on-chip columns in accordance with embodiments of the present invention.

FIG. 8 shows one type of the beads used for packing and testing. The beads of FIG. 8 are 7 µm-diameter anion exchange resin (PolyStyrene-Divinylbenzene beads with Trimethyl-Ammonium groups) from the Hamilton Company of Reno, Nev. The resins are the same as the resins in Hamilton's widely-used anion exchange column PRP-X110. FIG. 2(*c*) shows a section of on-chip column packed with the beads shown in FIG. 8.

Flow rate versus pressure curve is obtained after column is packed at 200 psi. The sample injection inlet (#3) and outlet (#4) are sealed with epoxy before measurement. DI water is pumped through column under constant pressure and flow rate is measured at column outlet by measuring liquid front moving speed in a capillary.

Figure 9:
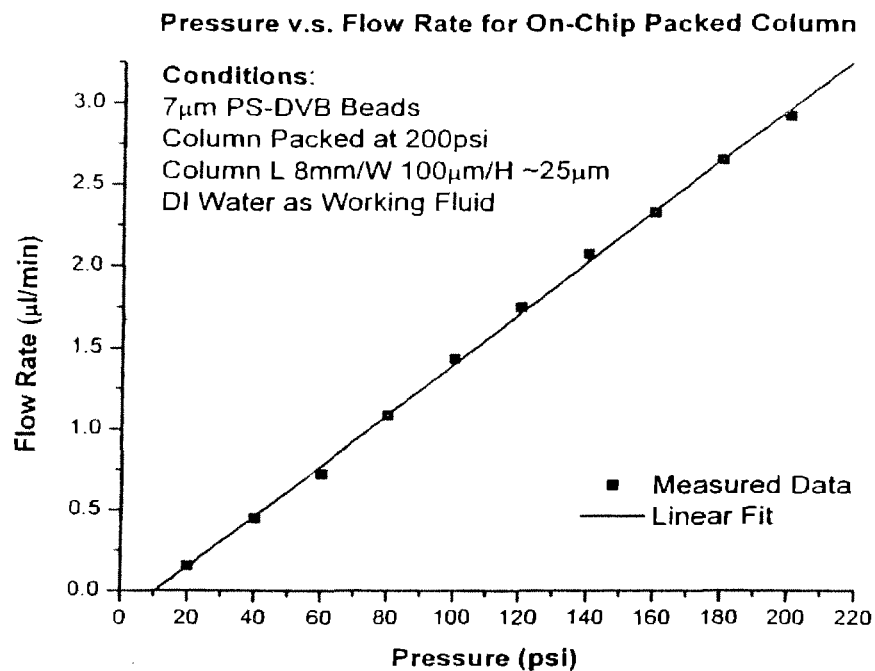
FIG. 9 plots on-chip packed column flow rate versus pressure measurement.

The volumetric flow rate is plotted against corresponding pressure in FIG. 9. It can be seen that the packed column provides huge back pressure, as the flow rate through the on-chip column is only about 3 µl/min even at 200 psi.

According to the theory set forth by Meyer, *Practical High Performance Liquid Chromatography*, John Wiley & Sons, pp. 310-311 (1999), incorporated by reference for all purposes herein, the following equation governs volumetric flow rate:

$$F = \frac{\varepsilon}{\phi} \frac{d_p^2 A_c}{\eta L_c} \Delta P;$$

where
F=volumetric flow rate;
ΔP=column pressure drop;
ε=porosity of packed column;
η=viscosity of the fluid;
$d_p$=beads diameter;
Φ=dimensionless flow resistance;
$A_c$=column cross-sectional area; and
$L_c$=column length.

From the fitted linear curve of FIG. 9, it is found that Φ/ε=444. Assuming the porosity of the packed column is 0.8, which is normal for densely-packed porous-spherical-beads column, then Φ is 355, which is close to but smaller than its empirical value of 500 for slurry packed spherical porous-beads in conventional LC columns. It is believed that this is partly due to the small on-chip column to bead size ratio.

Cross-channel injection method described above is used for injecting nanolitre/picolitre-volume samples into the column. Basically, this method limits flow path by controlling valves connected to the access holes of the system. During normal mobile phase flow, the valves controlling flow through points #3 and #4 (FIG. 1(a)) for the side injection channels are closed. During injection, the valve controlling flow through points #1 and #2 for the main flow path are closed, and the valves controlling flow through points #3 and #4 are open. Sample is injected from #3 to #4. The injected sample plug size is determined by the distance between the side channels, so that nanolitre-volume or even picolitre sample injection is easily achieved. Detailed discussion of the method can be found in the O'Neill et al publication incorporated by reference above.

The valves can be configured in different ways to perform various functions, some of which are summarized in Table 2.

TABLE 2

|  | CONFIGURATION OF VALVE AT POINT # | | | |
| --- | --- | --- | --- | --- |
|  | #1 | #2 | #3 | #4 |
| Packing | ○ | ○ | X | X |
| Sample Flush | X | X | ○ | ○ |
| Mobile Phase Flush | ○ | ○ | X | X |
| Sample Injection | X | X | ○ | ○ |

TABLE 2-continued

|  | CONFIGURATION OF VALVE AT POINT # | | | |
| --- | --- | --- | --- | --- |
|  | #1 | #2 | #3 | #4 |
| Elution | ○ | ○ | X | X |
| Flush Column | ○ | ○ | X/○ | X/○ |
| Flush Injection Loop | ○ | X | ○ | ○ |

Interdigitated Pt/Ti electrodes are used in the on-chip detection cell, which is located immediately after the on-chip chromatography column. The electrodes are used to monitor solution conductivity. When separated sample peaks flow through the detection cell, fluctuations in solution conductivity are recorded. AC signal is used for measuring conductivity. To determine an optimal frequency, the impedance frequency response curve is measured for the mobile phase solution.

Figure 10:
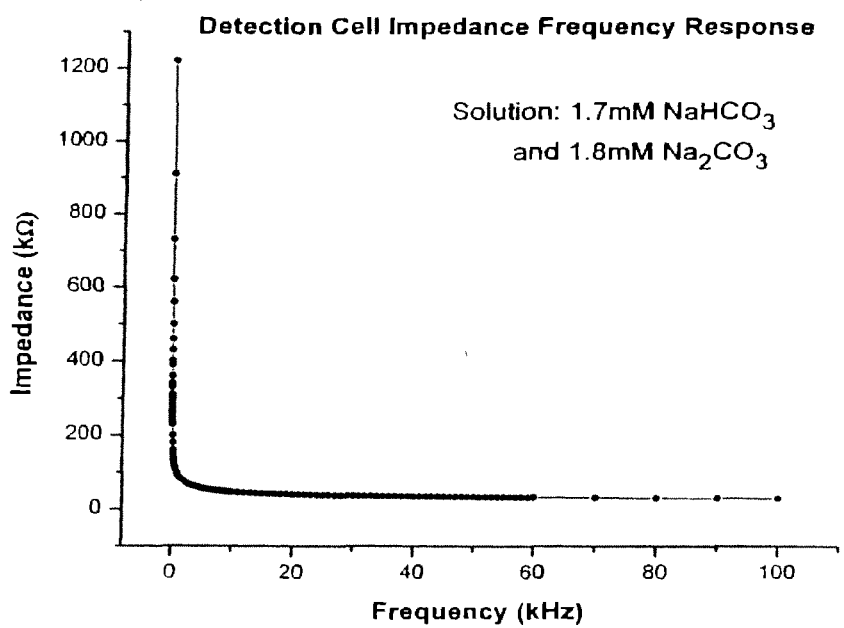
FIG. 10 plots impedance frequency response of the conductivity detection cell.

FIG. 10 shows impedance frequency response of the conductivity detection cell. The curve indicates that above about 10 kHz, the impedance is almost independent of frequency. Per Böhm et al., "A Closed-loop Controlled Electrochemically Actuated Micro-dosing System", *Journal of Micromechanics and Microengineering,* 10 498-504 (2000), incorporated by reference herein for all purposes, it is adequate for conductivity-measuring frequency to be in this resistance dominant region to minimize electrochemical effects.

To demonstrate on-chip liquid chromatography separation, ion-exchange LC is used partly because it is easy to verify separation using on-chip conductivity sensor. Anion mixtures in water with known concentrations have been successfully separated and detected with the on-chip conductivity sensor.

Figure 12:
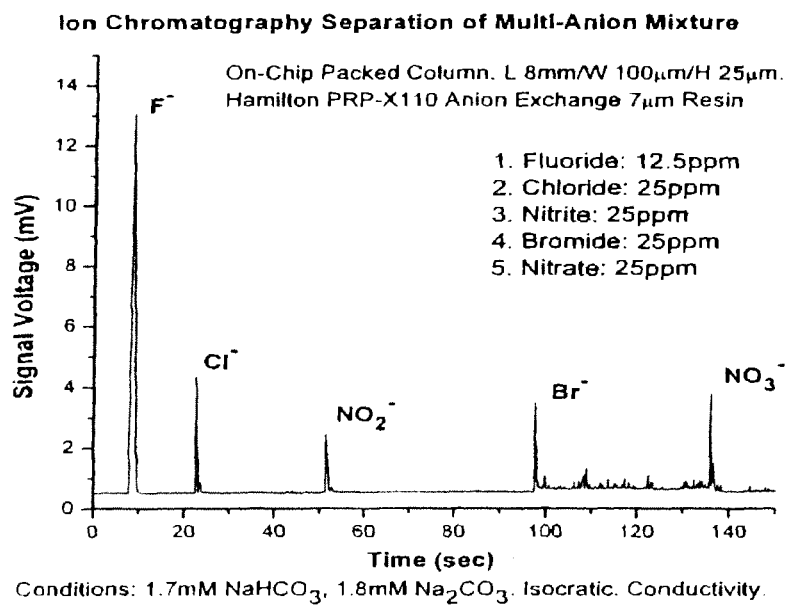
FIG. 12 shows ion-exchange liquid chromatography separation and detection of five anions in water using integrated nano-LC system on-a-chip.
Figure 13:
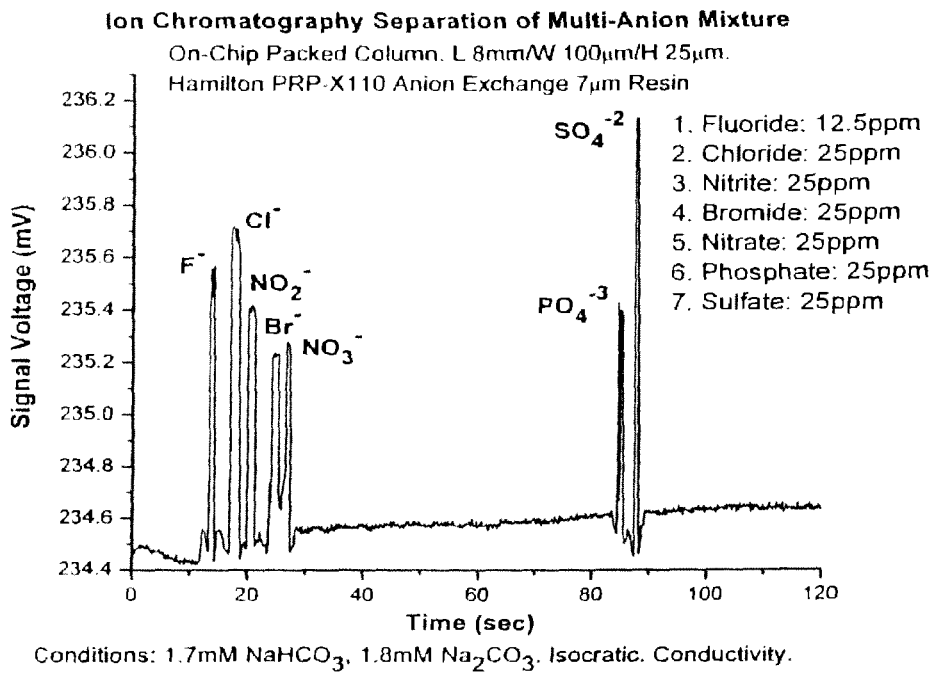
FIG. 13 shows ion-exchange liquid chromatography separation and detection of seven anions in water using integrated nano-LC system on-a-chip.

The on-chip column had a length of 8 mm, a width of 100 µm, and a height of 25 µm. The column was packed with PRP-X110 anion exchange 7 µm resin. Standard 1.7 mM $NaHCO_3$ and 1.8 mM $Na_2CO_3$ (Alltech Inc.) is used as mobile phase pumped at 0.2 µl/min isocratic with conductivity sensing. The injection volume is from 3 nl to tens of nanolitres. The chromatograms of FIGS. 11-13 show the typical ion exchange separation results.

Figure 11:
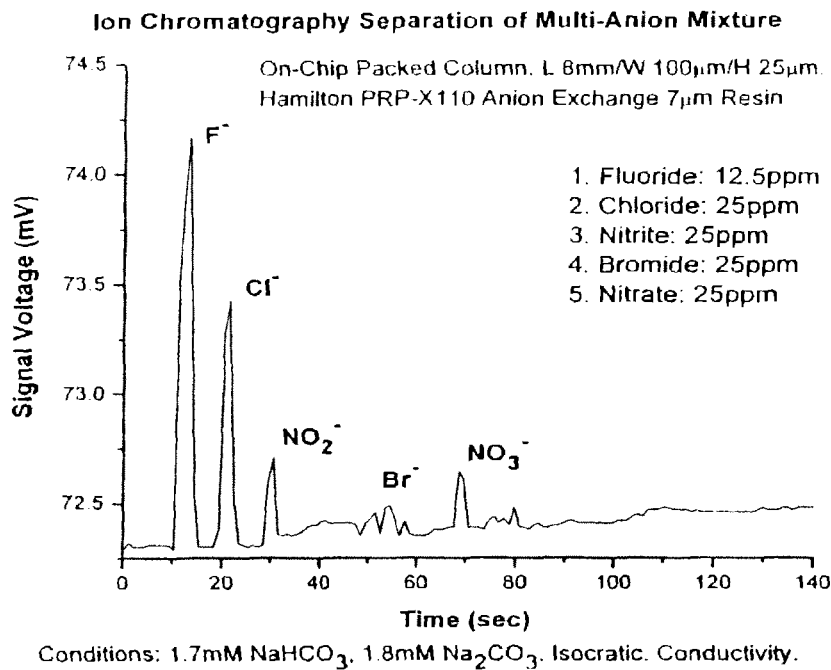
FIG. 11 shows ion-exchange liquid chromatography separation and detection of five anions in water using integrated nano-LC system on-a-chip.

Specifically, FIG. 11 shows ion-exchange liquid chromatography separation and detection of five anions in water using integrated LC system on-a-chip. The chromatogram of FIG. 11 was obtained using the basic measuring circuit. FIG. 12 shows ion-exchange liquid chromatography separation and detection of the same five anions in water with the integrated nano-LC system on-a-chip, using the basic measuring circuit plus lock-in amplifier.

Qualitative determination of the anions can be done by comparing the peak elution time or retention factors to those of the standard chromatogram. Or if one of the peaks can be confirmed by other methods, for instance electrochemical technique, then other peaks can be deduced.

Quantitative determination of the sample concentrations can be obtained by comparing the peak height/area to standard calibration curve, where the peak height/area is plotted against samples concentrations. This plot is typically linear. Table 3 shows a typical peak-analysis result of the chromatogram shown in FIG. 12, which includes integrated peak areas, peak-area percentage, peak center positions, peak heights and peak resolutions with respect to next peak.

TABLE 3

| Peak # | Anion | Area Integration | Area Percentage | Peak Center | Peak Height | Resolution w/Next Peak |
|---|---|---|---|---|---|---|
| 1 | Fluoride | 10.77885 | 52.19% | 8.622 | 11.7984 | 7.20554 |
| 2 | Chloride | 1.24881 | 6.05% | 22.672 | 1.58945 | 14.72439 |
| 3 | Nitride | 1.12842 | 5.46% | 51.435 | 1.0591 | 24.99618 |
| 4 | Bromide | 5.54006 | 26.82% | 97.713 | 1.09348 | 20.45866 |
| 5 | Nitrate | 1.95858 | 9.48% | 135.858 | 3.01061 | — |

Figure 14:
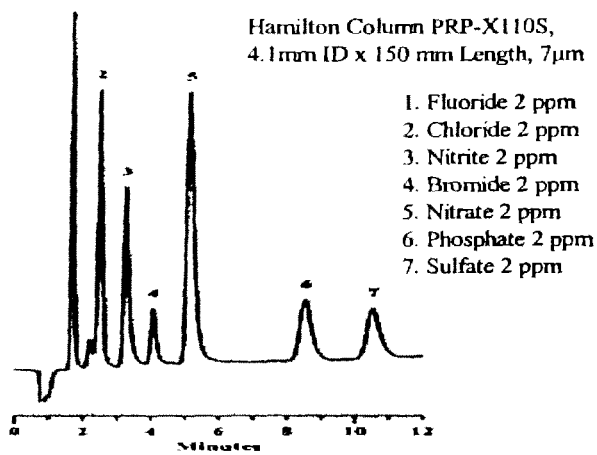
FIG. 14 shows separation of common anions using a commercial ion-exchange column and commercial ion liquid chromatography system.
Figure 15:
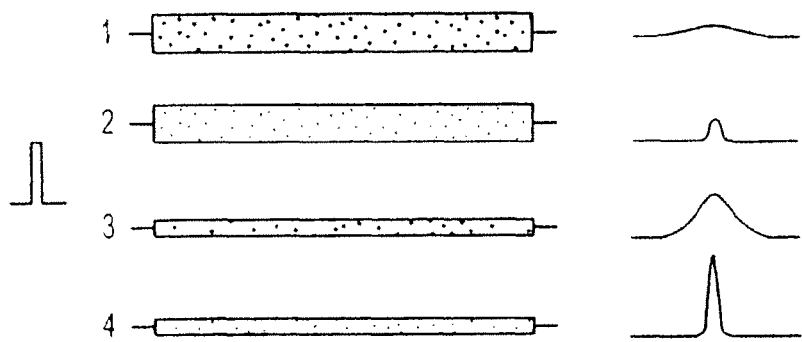
FIG. 15 shows separated peak shapes obtained with different column and bead size.

FIG. 13 shows the result of ion-exchange liquid chromatography separation and detection of seven anions in water using integrated LC system on-a-chip using the basic measuring circuit only. The results of FIG. 13 may be compared with FIG. 14, which shows separation of the same seven common anions using the commercially available PRP-X110S ion-exchange column from Hamilton Corp. having an inner diameter of 4.1 mm and a length of 150 mm. The beads used in this commercial column are the same used in the on-chip column separations.

To summarize, main obstacles previously encountered in miniaturizing LC systems include the lack of (1) a process to integrate various components of an LC system onto a monolithic chip; (2) high-pressure microfluidics needed for pumping liquid through densely-packed beads column; and (3) an approach to easily and reliably pack and seal chromatography supports (micro-beads) into the on-chip column.

Various embodiments in accordance with the present invention address all of the three problems. Integrated Parylene microfluidics technology is used to fabricate the device. Channel-strengthening techniques are invented to fulfill high-pressure requirements. Slurry technique is employed to pack beads externally into the on-chip column. U.S. non-provisional patent application Ser. No. 10/391,122, incorporated herein by reference for all purposes, describes an alternative method for integrating beads into microfabricated columns using batch fabrication process.

The invented chip is an integrated Parylene microfluidic system. The fabrication process is compatible with previously developed other Parylene microfluidic components, which can be integrated with the current chromatography system to provide more powerful liquid manipulation capability and also more separation and detection options, for example gradient separation and mass spectrometry detection.

The previously developed components include at least the following: gradient-generating electrolysis micro-pump, electrolysis micro-pump, peristaltic micro-pump, electrospray nozzle, micro-check valve, micro in-channel check valve, pressure sensors, flow sensors and shear stress sensor. These previously-developed components are described in the following reference list.

Xie, et al., "Integrated Parylene Electrostatic Peristaltic Pump", 7th Int'l. Syrup. on Micro Total Analysis System, California (µTAS 2003). Shih et al., "Surface Micromachined and Integrated Capacitive Sensors For Microfluidic Applications", 12th Int'l. Conf. on Solid-State Sensors, Actuators and Microsystems, pp. 388-391, Boston (Transducers 2003). Meng et al., "A Parylene MEMS Flow Sensing Array", Transducers 2003; Xie et al., "Electrolysis-Based On-Chip Dispensing system for ESI-MS", 16th IEEE Int'l MEMS Conf., Japan pp. 443-446 (MEMS '03). Xie et al., "Integrated Surface Micromachined Mass Flow Controller", (MEMS 2003). Meng et al., "A MEMS Body Fluid Flow Sensor", California (µTAS 2001). Xie et al., "Surface Micromachined Leakage Proof Parylene Check Valve", 14th IEEE International Conference on MicroElectroMechanical Systems, Switzerland, pp. 539-542 (MEMS '01). Wang et al., "A Normally Closed In-Channel Micro Check Valve", 13th IEEE International Conference on MicroElectro Mechanical Systems, Japan (MEMS '00). Wang et al, "A Parylene Micro Check Valve", 12th IEEE International Conference on Micro Electro Mechanical Systems (MEMS '99). Wang et al., "A Fully Integrated Shear Stress Sensor", 10th Int'l Conf. on Solid-State Sensors, Actuators and Microsystems (Transducers '99). Each of these references is incorporated by reference herein for all purposes.

Furthermore, the fabrication processes in accordance with embodiments of the present invention are also compatible with post-CMOS Integrated Circuits (IC) processes. In particular, the temperature during fabrication typically does not exceed 200° C. By remaining comfortably below the 600° C. threshold temperature resulting in the melting of interconnect metals such as aluminum, potentially the whole testing circuit, signal conditioning and processing, and even wireless transmission and power generation, could be integrated on the nano-liquid chromatography chip.

The on-chip column can be packed with any desired chromatography supports. Therefore, all kinds of LC can be done with the invented chip. Since the chip has on-chip injector and detector, fittings and tubing connecting injector and column, column and detector, are eliminated. The injected plug is right at the column inlet, and the separated components enter the detector right at the column outlet, which minimizes extra-column band broadening. Using on-chip injector, nanolitre or even picolitre size injection is easily achieved, which is extremely difficult for conventional off-chip injection methods.

The micro liquid chromatography chip is made using batch fabrication process, which reduces its cost dramatically, making disposable nano-LC chip possible. The solvent/sample consumption is also lowered considerably. High throughput separations can also be done by integrated multiple columns on-chip, as every column only takes small space on-chip. By packing the columns with different LC supports, various types of nano-LC can be done on-chip simultaneously.

The foregoing discussion of the invention has been presented for purpose of illustration and description. The foregoing is not intended to limit the invention to the form or forms disclosed herein. Possible variations of the system include, but not limited to the following alternative described embodiments.

Fabrication of the device is not limited to the specific embodiments described above in connection with FIGS. 3(a)-(h) and 4(a)-(h). For example, for faster fabrication, KOH or a combination of KOH and DRIE can be used to etch backside holes.

Moreover, in the process flows of FIGS. 3(a)-(g) and 4(a)-(g), the backside two-step access holes are used as a tubing stopper if tubing is to be directly inserted into the holes and bonded to chip backside. If, however, other packaging methods are used such as an O-ring seal, then a straight DRIE hole would be sufficient.

Moreover, the channel access holes are not required to be positioned on the device backside, but could alternatively be positioned on the device frontside. In such an alternative embodiment, holes to gain access to the channel portions could be created by punching or etching through the frontside Parylene layer, and also through any overlying passivation layer And while the filter has been shown as being fabricated by partial exposure, this is not required by the present invention. Other techniques may be utilized to hold the beads by restricting at least one dimension (width and/or height) in the flow path, and still remain within the scope of the present invention. One example is the fabrication of an array of posts to form a column frit/filter.

Moreover, while the specific process flow described above has utilized Parylene and photoresist as structural and sacrificial materials, respectively, other materials can be utilized to fabricate the channels. In addition, the substrate can be formed from other materials as well, including but not limited to silicon, glass, Pyrex, quartz, fused silica, polymer, and silicon-on-insulator (501).

And while the above description relates to the use of SU-8 as a passivation material, this is also not required by the present invention. In accordance with alternative embodiments, simple epoxy or other types of coating materials can be applied on top of the device to strengthen the channels and to provide passivation.

In accordance with still other embodiments of the present invention, dimensions of different features of the device, such as the shape, height, width, or length of the channel, can be adjusted for different applications. The filter height can also be varied for use with different bead sizes. Moreover, the configuration or size of the injection channels can also be adjusted.

In accordance with still other embodiments of the present invention, variation on the manner of sample injection may be employed. In accordance with alternative embodiments the sequence of operation of the valves can be changed, in order to achieve different injection performance. In accordance with still other alternative embodiments, different on-chip injection methods can also be used, for example, on-chip electrolysis-based sample injection.

In accordance with still other embodiments of the present invention, the column can be packed utilizing methods other than the slurry technique described above. In some embodiments, an open column can be used instead of a packed column. Such an open column can be coated with chromatography stationary phase materials as a separation support.

Various types of pumping methods can be used, including but limited to off-chip pumping with pressurized gas or a syringe pump, on-chip pressure-driven pumping, and/or electrically-driven pumping. Incorporated by reference herein for all purposes is U.S. nonprovisional patent application Ser. No. 10/391,122, incorporated by reference above, describes an on-chip electrolysis-based gradient pump capable of performing isocratic/gradient LC separations.

A variety of types of different devices may be in fluid communication with the outlet of the column, and remain within the scope of the present invention. For example, an electrospray nozzle can be integrated at the column outlet to couple the chip with Mass Spectrometer. Other detection methods can also be employed, for example, optical detection such as UV or fluorescence, can be performed in the detector cell. And since the fabrication process is post-CMOS compatible, various detecting, measuring, signal processing, and transmission circuits can readily be integrated on-chip.

In accordance with still further alternative embodiments of the present invention, the cross-sectional profile of the column may be determined by the particular fabrication process. Specifically, LC separation performance depends on the packing quality of the beads or other stationary phase within the column. A column having a rounded cross-sectional profile is generally preferred to one exhibiting a rectangular profile, as such a rectangular profile the latter leaves more dead volume near the inner side of the column when packed with spherical LC beads. Since microfabricated columns have an even smaller column ID to bead diameter ratio, this effect could be more pronounced for nano LC columns. Therefore, under certain circumstances it may be desirable to fabricate micromachined columns having rounded cross-sections.

Conversely, in other applications, a rectangular micromachined column, or a column exhibiting some combination of the rounded and rectangular cross-sectional profile, may be desired. For example, microfabricated devices frequently employ optical detection based upon the simplicity and sensitivity of this sensing technique. With microfabricated nano-LC columns exhibiting circular cross-sections, light incident for detection purposes may be undesirably deflected when passing through the column wall. Such unwanted optical deflection would not occur for microfabricated columns exhibiting a cross-sectional profile that is wholly rectangular, or partially rectangular at the location of transmission of the optical sensing beam.

Therefore, in an alternative embodiment of a fabrication method in accordance with the present invention, the nano-LC column may be tailored to exhibit a cross-sectional or rectangular profile for different applications. Specifically, during formation of the column, sacrificial material can formed in a rounded cross-sectional profile.

The basic idea utilizes a thermal reflow property of a sacrificial material, typically a photoresist. The sacrificial material used to define the column can be thermally reflowed after photo-patterning (FIG. 3(c) or 4(c)), but before deposition of the Parylene (FIG. 3(e) or 4(e)). The higher the temperature and/or the longer the baking, the more rounded the cross-section will be obtained. To demonstrate the effect, two nano-LC columns with different cross-sections, one nearly rectangular and the other nearly circular, were fabricated.

Figure 17A:
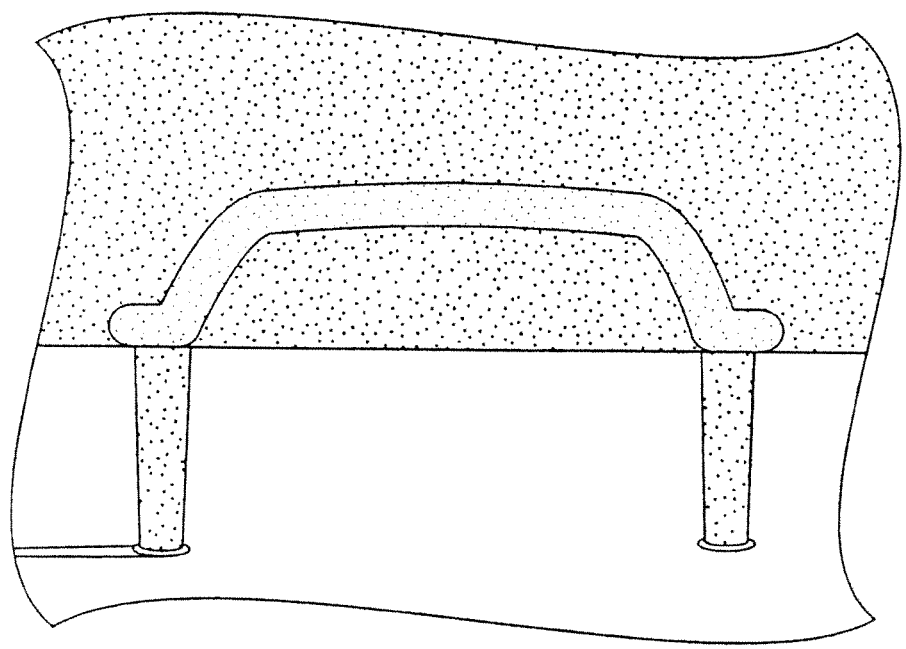
FIG. 17(a) shows a photograph of a microfabricated nano-LC column in accordance with an embodiment of the present invention, exhibiting a nearly-rectangular cross-sectional profile.
Figure 17B:
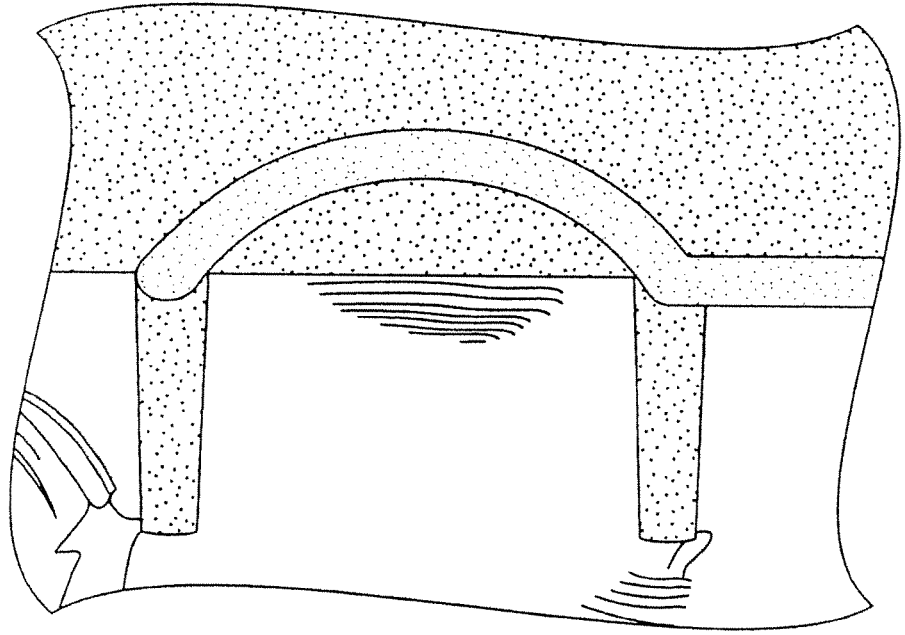
FIG. 17(b) shows a photograph of a microfabricated nano-LC column in accordance with an embodiment of the present invention, exhibiting a rounded cross-sectional profile.

FIG. 17(a) shows a photograph of a nano-LC column microfabricated without thermal reflow and exhibiting a nearly rectangular cross-sectional profile. FIG. 17(b) shows a photograph of another nano-LC column microfabricated to have a rounded cross-section by thermal reflow of its column sacrificial photoresist during processing before parylene deposition. FIGS. 17(a)-(b) illustrate that the cross-sectional profile of the nano-LC column can be tailored for different applications.

In accordance with still another alternative embodiment of the present invention, the sensitivity of the detector can be improved utilizing background suppression integrated on-chip. Specifically, a conductivity detector records a baseline solution conductivity during elution of the liquid phase, when no sample ion is passing by. The conductivity detector will detect a change of conductance when a sample ion is eluted from the column and enters the detector cell. This detected conductivity change will be manifested as a peak or valley superimposed on the baseline signal. The magnitude of this conductivity signal is proportional to the difference in conductance between the total eluted solution and the background, as expressed in the following equation:

$$\Delta G = G_{Elution} - G_{Background} = \frac{1000}{K_{cell}}(\lambda_{S^-} - \lambda_{E^-})C_S$$

$G_{Elution}$: Total conductance of the eluted solution
$G_{Background}$: Background conductance of the eluent
$K_{cell}$: Cell constant of the conductivity sensor
$\lambda_{S^-}$: Equivalent conductance constant for sample ion
$\lambda_{E^-}$: Equivalent conductance constant for eluent ion
$C_S$: Concentration of the sample ion to be detected Normally, the peak of the conductance signal lies only a few percent over the background signal. This is especially true for ppm (pan-per-million) and ppb (part-perbillion) level sensing. Moreover, the eluent used in ion liquid chromatography typically exhibits a high conductivity, making the detection of low-concentrations of Ions difficult.

Conventionally, this sensitivity issue has been addressed by introducing a chemical suppression device between the outlet of the separation column and the inlet of the detector. Such a chemical suppression device reacts with the solution eluted from the column, reducing its conductivity to nearly zero prior to entry into the detector. By performing this conventional background suppression, the detection limit of the LC system can usually be lowered by about three orders of magnitude.

Figure 18:
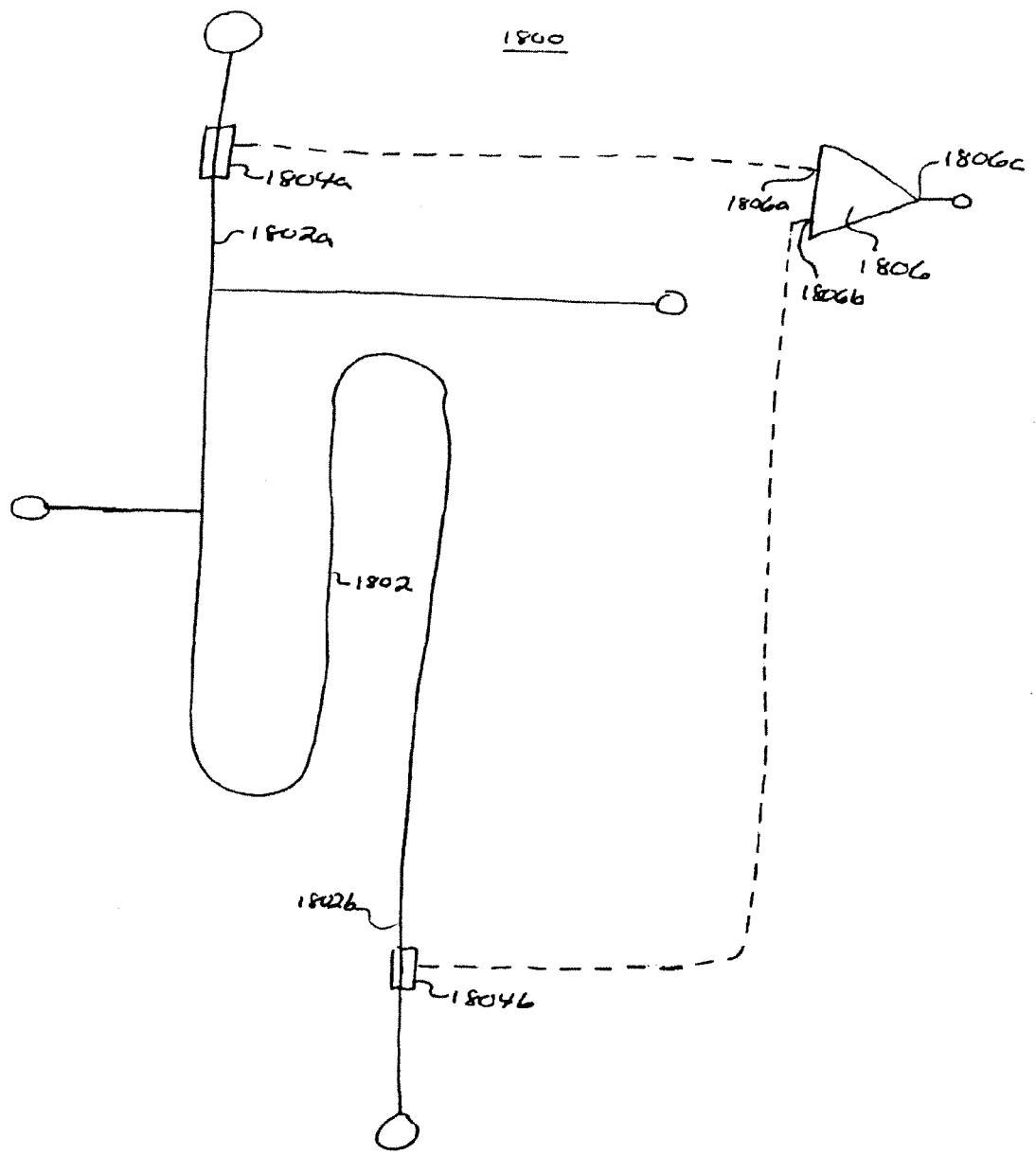
FIG. 18 shows simplified plan view of an alternative embodiment of a microfabricated nano-LC system in accordance with the present invention, utilizing on-chip electronic background suppression.

An alternative embodiment in accordance with the present invention integrates on-chip an electronic suppression method that will remove the background conductance from the total signal. FIG. 18 shows a simplified schematic plan view of such an embodiment of a nano-LC system in accordance with the present invention.

Nano-LC system 1800 of FIG. 18 comprises microfabricated column 1802 having inlet 1 802a and outlet I 802b. Nano-LC system 1800 further comprises two conductivity detectors having the same structure formed on-chip at different locations. First conductivity detector 1804a is located upstream of the point of sample introduction, and is configured to measure background conductance only. Second conductivity detector 1804b is located downstream of the column outlet and measures the total conductance of the solution eluted from column, including both sample and solvent.

Both the first and second conductivity detectors 1804a and 1804b are in electrical communication with comparator 1806. Comparator 1806 comprises input nodes 1806a and 1806b, configured to receive signals from detectors 1804a and 1804b, respectively. Comparator 1806 is configured to output at node 1806c an amplified signal reflecting the difference between the two sensors' response.

An embodiment of a nano-LC system utilizing background suppression offers a number of potential benefits. One such benefit is the effective suppression of the background signal, allowing the detection limit to be lowered by several orders of magnitude.

Another potential benefit is ease of fabrication. Specifically, a system including the additional conductivity sensor can easily be integrated within an existing fabrication scheme such as is shown in FIGS. 3(a)-(h) or 4(a)-(h), requiring only changes to the mask layout without requiring additional steps that could result in lower throughput and increased expense.

Further variation on specific embodiments of the present invention shown and discussed so far are possible. For example, an alternative embodiment in accordance with the present invention could utilize a flow path comprising multiple successive columns employing different packing media or separation chemistry to perform multi-dimensional separations. Still other alternative embodiments could utilize a flow path comprising multiple parallel columns employing different packing media or separation chemistry to simultaneously perform multiple separation of the components of multiple samples. In accordance with still other embodiments, a single chip could include a plurality of columns configured to perform separations to isolate components of multiple samples, and also to conduct multi-dimensional separation to isolate components of a single sample.

The small size of embodiments of nano-LC devices in accordance with the present invention, coupled with their ability to perform chemical/biological sensing on-chip, renders them suitable for use in a variety of applications. In particular, employment of component separation techniques upstream of detection, reduces or eliminates the need to provide specialized detection devices of limited applicability to only certain target materials. Thus nano-LC devices in accordance with embodiments of the present invention are suitable for uses such as monitoring of the environmental condition of remote sites, networked sensing, and consumer health care.

It is to be understood that the examples and embodiments described herein are for illustrative purposes only, and there can be other variations and alternatives. Various modifications or changes in light of the above description thereof will be suggested to persons skilled in the art and are to be included within the spirit and purview of this application and scope of the appended claims.

What is claimed is:

1. A method of fabricating a high pressure nano-liquid chromatography system on-a-chip, the method comprising:
    providing a substrate having a front first side and having a back second side; wherein the substrate has a layer disposed on the front first side;
    etching in two places the substrate from the back second side to form two holes and two diaphragm regions in the substrate adjacent to the holes; wherein the two diaphragm regions have the layer disposed on the front first side disposed on two diaphragms;
    from the front first side, etching the layer disposed on the front first side above the two diaphragm regions in the substrate to remove the layer over the diaphragms;
    patterning a sacrificial material on the front first side of a substrate to define a column region which covers the diaphragm regions,
    forming an encapsulant over the front first side of the substrate and the sacrificial material; wherein forming the encapsulant comprises depositing Parylene, and prior to deposition of Parylene, a moat is etched into the substrate adjacent to the channel to receive and anchor the deposited Parylene;
    etching through the diaphragm regions from the back second side to open an inlet hole and an outlet hole;
    removing the sacrificial material defining a column region through the inlet hole and the outlet hole to form the column region,
    wherein the method further comprises forming a epoxy passivating layer over the encapsulant,
    wherein the system provides a pressure limit of 1000 psi or greater.

2. The method of claim 1 wherein:
    patterning the sacrificial material comprises developing a resist material utilizing lithography; and
    removing the sacrificial material comprises stripping the developed resist material.

3. The method of claim 2 wherein patterning the sacrificial material further comprises partially developing the resist material to define a constriction at the column outlet.

4. The method of claim 3 wherein the constriction comprises an opening narrower than a column packing material.

5. The method of claim 2 wherein patterning the sacrificial material further comprises patterning a post to define a constriction at the column outlet.

6. The method of claim 1 wherein the moat etching is self-aligned to the sacrificial material.

7. The method of claim 1 wherein prior to deposition of the Parylene, regions adjacent to the channel are roughened by chemical exposure to enhance adhesion with the deposited Parylene.

8. The method of claim 7 wherein the roughening is self-aligned to the sacrificial material.

9. The method of claim 1 wherein the passivating layer is formed subsequent to removal of the sacrificial material.

10. The method of claim 1 wherein the passivating layer is formed prior to removal of the sacrificial material.

11. The method of claim 1 further comprising patterning a conducting electrode on the substrate proximate to an expected outlet of the column, prior to patterning the sacrificial material.

12. The method of claim 1 wherein the sacrificial material is also patterned to form a sample injector region intersecting the column region, the method further comprising providing access to an inlet of the injector region and to an outlet of the injector region.

13. The method of claim 1 wherein a temperature during fabrication does not exceed 200° C.

14. The method of claim 1 further comprising introducing a packing material into the column.

* * * * *

UNITED STATES PATENT AND TRADEMARK OFFICE
CERTIFICATE OF CORRECTION

| | | |
|---|---|---|
| PATENT NO. | : 9,288,915 B2 | Page 1 of 1 |
| APPLICATION NO. | : 13/680030 | |
| DATED | : March 15, 2016 | |
| INVENTOR(S) | : Yu-Chong Tai et al. | |

It is certified that error appears in the above-identified patent and that said Letters Patent is hereby corrected as shown below:

IN THE SPECIFICATION

IN COLUMN 1, LINES 20-25, SHOULD READ, UNDER THE HEADING:

STATEMENT AS TO RIGHTS TO INVENTIONS MADE UNDER FEDERALLY SPONSORED RESEARCH OR DEVELOPMENT

--This invention was made with government support under Grant No. RR06217 awarded by the National Institutes of Health and under Grant No. 0121778 and Grant No. 9402726 awarded by the National Science Foundation. The government has certain rights in the invention.--

Signed and Sealed this
Seventh Day of June, 2016

Michelle K. Lee
*Director of the United States Patent and Trademark Office*